(12) United States Patent
Abe (10) Patent No.: US 9,797,997 B2
(45) Date of Patent: Oct. 24, 2017

(54) ULTRASONIC DIAGNOSTIC SYSTEM AND SYSTEM AND METHOD FOR ULTRASONIC IMAGING

(75) Inventor: Yasuhiko Abe, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1144 days.

(21) Appl. No.: 11/336,958

(22) Filed: Jan. 23, 2006

(65) Prior Publication Data
US 2006/0122512 A1 Jun. 8, 2006

Related U.S. Application Data

(63) Continuation of application No. PCT/JP2005/009966, filed on May 31, 2005.

(30) Foreign Application Priority Data

May 31, 2004 (JP) .................................. 2004-161794

(51) Int. Cl.
*A61B 8/00* (2006.01)
*G01S 7/52* (2006.01)
(Continued)

(52) U.S. Cl.
CPC ........ *G01S 7/52071* (2013.01); *A61B 8/0883* (2013.01); *A61B 8/488* (2013.01);
(Continued)

(58) Field of Classification Search
USPC ........................................ 600/453, 441, 443
See application file for complete search history.

(56) References Cited

U.S. PATENT DOCUMENTS 4,463,763 A    8/1984  Koyano et al.
5,622,174 A *  4/1997  Yamazaki ..................... 600/441
(Continued)

FOREIGN PATENT DOCUMENTS

CN    1106825 C    4/2003
JP    6-114059 A   4/1994
(Continued)

OTHER PUBLICATIONS

Shinji Oshita et al., "Choonpa Shin-echo Kinetic Gazo Shori ni yoru Shinkino no Jido Shikibetsuho", The Transactions of the Institute of Electronics, Information and Communication Engineers A, Dec. 1, 2001 (Dec. 1, 2001), vol. J84-A, No. 12, pp. 1461 to 1468.
(Continued)

*Primary Examiner* — Sanjay Cattungal
*Assistant Examiner* — Bradley Impink
(74) *Attorney, Agent, or Firm* — Oblon, McClelland, Maier & Neustadt, L.L.P.

(57) ABSTRACT

The ultrasonic diagnostic system estimates a desired time phase or one cycle period of a moving region (e.g., a heart) that repeats contraction and relaxation cyclically and which can be specified by a presystole, an end systole, a prediastole, an end diastole, and other clinical characteristics for one cycle of the moving region on the basis of the velocity information on multiple positions of the moving region which is obtained for each time phase. More specifically, assuming that, for example, the end systole phase=a time phase in which the myocardial velocity comes to zero or close to zero, the system calculates |myocardial velocity| for each time phase in a predetermined period, and estimates a time phase in which this value comes closest to zero as an end systole phase.

11 Claims, 7 Drawing Sheets

(51) Int. Cl.
*A61B 8/08* (2006.01)
*G06T 7/20* (2017.01)
*A61B 8/02* (2006.01)
*G01S 15/89* (2006.01)

(52) U.S. Cl.
CPC *G06T 7/20* (2013.01); *A61B 8/02* (2013.01); *A61B 8/485* (2013.01); *G01S 15/8979* (2013.01); *G06T 2207/30048* (2013.01)

(56) References Cited

U.S. PATENT DOCUMENTS

| | | | |
|---|---|---|---|
| 5,701,897 A * | 12/1997 | Sano | 600/453 |
| 5,785,654 A * | 7/1998 | Iinuma et al. | 600/441 |
| 6,638,221 B2 | 10/2003 | Abe et al. | |
| 2001/0024516 A1 | 9/2001 | Yoshioka et al. | |
| 2003/0083578 A1 * | 5/2003 | Abe et al. | 600/447 |
| 2003/0171668 A1 | 9/2003 | Tsujino et al. | |
| 2004/0116810 A1 * | 6/2004 | Olstad | A61B 8/0883 600/443 |
| 2005/0085729 A1 | 4/2005 | Abe | |

FOREIGN PATENT DOCUMENTS

| | | |
|---|---|---|
| JP | 8-182680 A | 7/1996 |
| JP | 9-140711 | 6/1997 |
| JP | 10-99328 | 4/1998 |
| JP | 10-262970 | 10/1998 |
| JP | 2001-70303 | 3/2001 |
| JP | 2003-175041 | 6/2003 |
| JP | 2003-250804 | 9/2003 |
| JP | 2004-73850 | 3/2004 |

OTHER PUBLICATIONS

Chinese Office Action issued Sep. 25, 2014, in China Patent Application No. 201110305820.8 (with English translation).

* cited by examiner

| HR [bpm] | t0 [msec] | tg [msec] |
|---|---|---|
| <50 | 300 | 100 |
| 50≤ <100 | 250 | 100 |
| 100≤ <200 | 200 | 100 |
| 200≤ | 150 | 100 |

ULTRASONIC DIAGNOSTIC SYSTEM AND SYSTEM AND METHOD FOR ULTRASONIC IMAGING

CROSS-REFERENCE TO RELATED APPLICATIONS

This is a Continuation Application of PCT Application No. PCT/JP2005/009966, filed May 31, 2005, which was published under PCT Article 21(2) in Japanese.

This application is based upon and claims the benefit of priority from prior Japanese Patent Application No. 2004-161794, filed May 31, 2004, the entire contents of which are incorporated herein by reference.

BACKGROUND OF THE INVENTION

1. Field of the Invention

The present invention relates to an ultrasonic diagnostic system and a system and a method for ultrasonic imaging wherein the velocity of biological tissue such as cardiac muscle is estimated, and the estimated velocity information is processed to output local motion information of the tissue, thereby providing information useful in medical diagnosis, and in particular, it relates to a method for reducing the time and labor for operation by automatically detecting an end systole phase.

2. Description of the Related Art

Objective and quantitative evaluation of functions of biological tissue is generally very important for diagnosis of biological tissue such as cardiac muscle. Diagnostic imaging using an ultrasonic imaging system also tries various quantitative evaluations principally for hearts as an example. A typical example is tissue tracking imaging (TTI) method (e.g., refer to Patent Document 1). The TTI method allows quantitative evaluation by local-wall-motion indices such as distortion and displacement using tissue velocity.

To find distortion or displacement using tissue velocity, time quadrature is required, as described in Patent Document 1. Since the result of time quadrature depends on an integration interval (time), the importance of the setting of the interval will easily be understood.

Of particular importance is a start phase. When integration start phase is, for example, in an end diastole phase, systolic distortion and displacement can be analyzed. Paying attention to distortion, normal cardiac muscle is thickened in the wall thickness direction (the minor axis), and shortened along the major axis during systole. In contrast, when the integration start phase is in end systole phase, diastolic distortion and displacement can be analyzed. Also paying attention to distortion, normal cardiac muscle is thinned in the wall thickness direction (the minor axis), and stretched along the major axis during systole.

Furthermore, integration end time is important second to the start time phase as a time phase that reflects the final state of distortion and displacement in specified intervals such as systole and diastole. Specifically, the most common way will be that the state of the whole motion by time quadrature for systole is analyzed in an end systole phase, and the state of the whole motion by time quadrature for diastole is analyzed in an end diastole phase.

To determine the integration interval for systole or diastole for a variety of applications, the end diastole phase and the end systole phase must be provided as accurately as possible. To enhance simplicity of the analyzing process, it is desirable that the two time phases of end diastole phase and end systole phase be set automatically. Furthermore, a technique of monopolar display of distortion is disclosed in JP-A-2003-175041, for example, as another unique application setting other than the setting of an integration interval in each phase interval of systole and diastole. To realize accurate and simple time phase setting is also very useful for the distortion monopolar display.

Of the end diastole phase and the end systole phase, the end diastole phase can be detected automatically as an R-wave phase in an electrocardiogram. On the other hand, the end systole phase cannot easily be detected from an electrocardiogram; however, the following automatic setting technique is known.

With stress echo packages, which are recently becoming widespread, only systoles are often cut out from a series of moving images, and are analyzed. In this case, a specified interval (duration time DT [sec]) from R wave can be set. Specifically speaking, a DT phase corresponds to an end systole phase. It is known that DTs vary depending on heart rates (HR) [bpm] (DTs decrease generally as HRs increase). Accordingly, DTs can often be set by users as a table for each HR.

Despite such devised stress echo packages, the accuracy required for an end systole phase being set is so low to be determined uniquely by a predetermined time in advance. Thus, since it has not a structure determined to the motion of a signal source, e.g., it is not necessarily a high-accuracy setting method for an end systole phase. Accordingly, this has the disadvantage of low time accuracy in view of automatically setting intervals of time quadrature for finding distortion or displacement.

Furthermore, a technique of automatically recognizing an end systole phase using a cardiac-cavity volume/area or cardiac sound graph by automated contour tracking (ACT) method is recently disclosed (e.g., refer to Patent Document 2). As shown in the document, it is generally known that "an end systole phase in clinical term is the time when the second sound on a phonocardiogram is generated". However, it is difficult to stably detect only the second sound from a phonocardiogram waveform having many abrupt changes, and there can be also some cases in which a phonocardiogram cannot always be provided at examinations (because many cardiac ultrasonic examinations use only phonocardiograms as reference signals). The technique by the ACT method discloses "finding an end systole phase as a time phase in which the area or volume of a cardiac cavity is minimized" by estimating the area or volume of a cardiac cavity from positional information on endocardium that is automatically detected.

BRIEF SUMMARY OF THE INVENTION

However, the ACT method cannot be applied to cross sections such as a longitudinal image of a left ventricle in which a cardiac cavity is not clearly drawn. To increase the accuracy of time for finding an end systole phase, it is preferable to obtain a cardiac-cavity volume with high accuracy. However, only one cross section allows definition of only an area, so that it is difficult to ensure an accurate volume. Multiple reference cross sections are generally required to obtain a high-accuracy volume. This is complicated technically, thus decreasing simplicity. Consequently, the ACT method cannot increase the accuracy and lacks in operability in setting cross sections because of its limitation to available cross sections.

The invention has been made in view of the above-described circumstances. Accordingly, it is an object of the invention to provide an ultrasonic diagnostic system and a system and a method for ultrasonic imaging capable of simple and high-accuracy automatic detection of end systole phases for all cross section images used in general cardiac ultrasonography.

According to a first aspect of the invention, an ultrasonic diagnostic system or an ultrasonic imaging system is provided which includes: a storage unit that stores time-series velocity information on a moving region that repeats contraction and relaxation cyclically; and an estimation unit that estimates any desired time phase for one cycle including the contraction and relaxation of the moving region based on the time-series velocity information.

According to a second aspect of the invention, a method for ultrasonic imaging is provided which includes: obtaining time-series velocity information on a moving region that repeats contraction and relaxation cyclically; and estimating any desired time phase for one cycle including the contraction and relaxation of the moving region based on the time-series velocity information.

DETAILED DESCRIPTION OF THE INVENTION

Embodiments of the invention will be described wither reference to the drawings. In the following description, components having the same function and structure will be given the same reference numerals and a duplicated description will be given as required.

Figure 1:
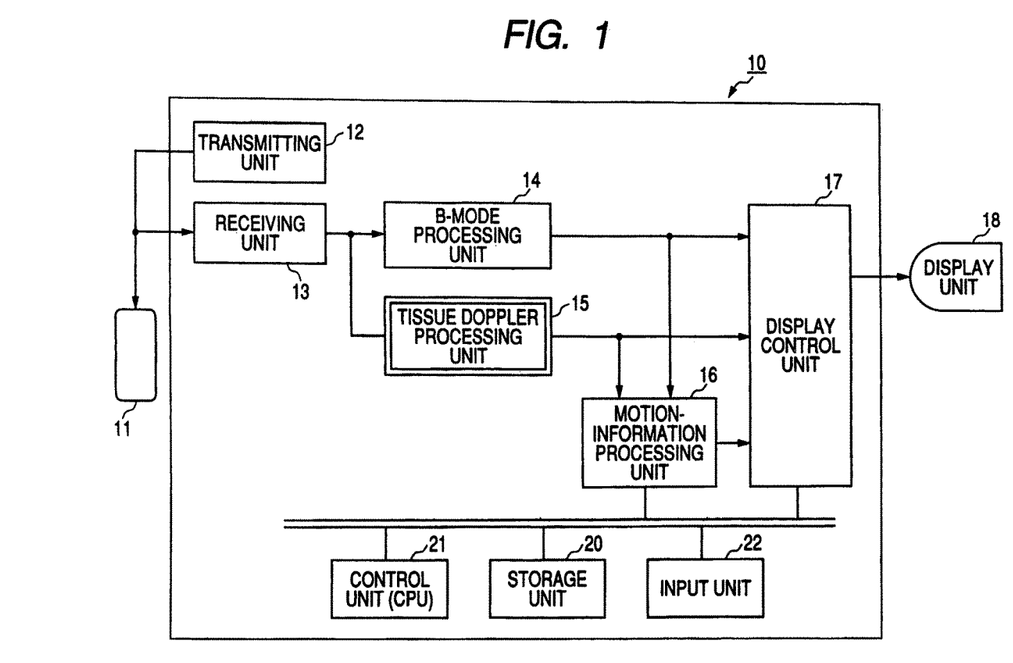
FIG. 1 is a block diagram of an ultrasonic diagnostic system 10 according to a first embodiment.

FIG. 1 is a block diagram of an ultrasonic diagnostic system 10 according to a first embodiment. The ultrasonic diagnostic system 10 includes an ultrasonic probe 11, a transmitting unit 12, a receiving unit 13, a B-mode processing unit 14, a tissue Doppler processing unit 15, a motion-information processing unit 16, a display control unit 17, a display unit 18, a storage unit 20, a control unit 21, and an input unit 22.

The ultrasonic probe 11 includes a plurality of piezoelectric vibrators that generates ultrasonic waves in response to a drive signal from the transmitting unit 12, and converts reflected waves from a subject to electric signals; a matching layer provided to the piezoelectric vibrators; and a backing material for preventing propagation of the ultrasonic waves from the piezoelectric vibrators to the back. When ultrasonic waves are transmitted from the ultrasonic probe 11 to the subject, various harmonic components are generated with the propagation of the ultrasonic waves owing to the non-linearity of biological tissue. The fundamental waves and harmonic components that constitute transmission ultrasonic waves are scattered backward by the boundary of acoustic impedance of in vivo tissue, microscattering etc., and are received by the ultrasonic probe 11 as reflected waves (echo). Since this embodiment and the following-described embodiments explain a case of a heart being an imaged object as an example, a sector probe is used as the ultrasonic probe 1.

The transmitting unit 12 includes a delay circuit and a pulser circuit (not shown). The pulser circuit repeatedly generates a rate pulse for forming transmission ultrasonic waves at a predetermined rate frequency fr Hz (cycle: 1/fr sec). The delay circuit provides each rate pulse with a delay time necessary for converging ultrasonic waves into a beam for each channel and determining transmission directivity. The transmitting unit 12 applies driving pulses to each vibrator at timing based on the rate pulses so that the ultrasonic beams are formed in the direction of a specified scan line.

The receiving unit 13 includes an amplifier circuit, an A/D converter, an adder and the like (not shown). The amplifier circuit amplifies the echo signal taken via the probe 11 channel by channel. The A/D converter provides a delay time necessary for determining reception directivity to the amplified echo signal, and thereafter, the adder performs adding process. The addition generates an ultrasonic echo signal corresponding to a specified scan line.

The B-mode processing unit 14 applies an envelope detection process to the ultrasonic echo signal received from the receiving unit 13 to thereby generate a B-mode signal corresponding to the amplitude intensity of the ultrasonic echo signal.

The tissue Doppler processing unit 15 applies an orthogonal detection process, an autocorrelation process, and so on to the echo signal received from the receiving unit 13 to obtain a tissue Doppler signal corresponding to the velocity, dispersion, and power of the tissue moving in the subject on the basis of the Doppler displacement component of the ultrasonic echo signal subjected to the delay and addition process.

The motion-information processing unit 16 executes various processes for obtaining a motion-information image on the basis of the B-mode signal output from the B-mode processing unit 14 and the Doppler signal output from the tissue Doppler processing unit 16.

The motion-information processing unit 16 also executes the process of estimating a desired time phase and the process of automatically setting an integration interval by TTI method, which will be described later, using velocity-distribution images stored in the storage unit 20.

The display control unit 17 generates a B-mode ultrasonic image indicative of the dimensional distribution of a B-mode signal on a specified cross section. The display control unit 17 also generates a tissue Doppler ultrasonic image indicative of a two-dimensional distribution of the velocity, dispersion, and power values on a specified cross section on the basis on the tissue Doppler signal. The display control unit 17 also generates a superimposed image of a B-mode ultrasonic image and a tissue Doppler ultrasonic image, a superimposed image of a B-mode ultrasonic image and a two-dimensional distribution image of displacement or distortion, and so on as needed.

The display unit 18 displays in-vivo morphological information and blood-flow information according to a video signal from the display control unit 17 as an image. When a contrast medium is used, the motion-information processing unit 16 displays a luminance image or a color image according to quantitative information on the spatial distribution of the contrast medium, that is, the area of blood flow or blood.

The storage unit 20 stores ultrasonic image data (ultrasonic reception data) corresponding to each phase, a velocity-distribution image corresponding to time phases generated by the motion-information processing unit 16, and so on. The ultrasonic image data assumes tissue-image data taken in a tissue Doppler mode and tissue-image data taken in other than the tissue Doppler mode. The tissue image data may be so-called raw image data before scan conversion.

The control unit 21 has the function of an information processor (computer), and controls the operation of the ultrasonic diagnostic system body statically or dynamically.

The input unit 22 is connected to the system 10, and includes various switch buttons (and/or a mode switch), a track ball, a mouse, a keyboard, and so on for bringing in various instructions from the operator, such as an instruction to set and change various parameters and conditions and an instruction to set a region of interest (ROI) to the system main body.

(Tissue Tracking Imaging)

Tissue tracking imaging method (TTI) that is the prerequisite technique of the embodiment will be briefly described. The tissue tracking imaging images the parameters of local displacement and distortion obtained by integrating a signal based on velocity information, as tissue-motion information, while tracking the position of tissue which changes with motion. The technique allows the image of the distortion and displacement of local cardiac muscle to be produced and displayed using, e.g., a minor-axis image, thus supporting the analysis of temporal changes in image output values for a local region. In the case of using the minor-axis image, the main object function of cardiac analysis is thickening (change in thickness). The tissue tracking imaging method adopts the concept of a contraction motion field directed to a contraction center and setting therefor to detect a component relating to the thickening by angular compensation and to image it. The tissue tracking imaging method is also applicable to a temporally variable motion field by temporally shifting the contraction center position in consideration of the effects of the translational motion (also referred to as "translation") of the entire heart. This consequently allows tracking to the variations of the contract center position due to translational motion. Further details of the tissue tracking imaging method is described in JP-A-2003-175041, for example. The contents of the reference will be added to the description of the embodiment.

The tissue tracking imaging method requires a space-time distribution image of tissue velocities for multiple phases (an image indicative of the velocities of the positions of tissue to be diagnosed). The space-time distribution image of the tissue velocities (hereinafter, simply referred to as "a velocity-distribution image") can be generated from two-dimensional or three-dimensional ultrasonic image data on multiple time phases collected by tissue Doppler imaging, or alternatively, can be obtained by giving pattern-matching to multiple two-dimensional or three-dimensional tissue images on multiple time phases collected by the B-mode processing unit or the like.

The embodiment uses a two-dimensional velocity distribution image produced by the tissue Doppler imaging (TDI) to provide a concrete description. However, the invention is not limited to that, but may use a three-dimensional velocity distribution image produced by tissue Doppler imaging, for example, or a two-dimensional or three-dimensional velocity distribution image produced by pattern matching. The embodiment uses a heart as a diagnostic object by way of example. Accordingly, most of tissue velocities obtained by tissue tracking imaging can be regarded as myocardial velocity.

(Time-Phase Estimating Function)

The time-phase estimating function of the ultrasonic diagnostic system 10 will be described. The time-phase estimation is for analytically estimating, for example, various time phases, which are clinically important, using phase-to-phase velocity distribution images stored in the storage unit 20. Although estimation of an end systole phase will be described below to simplify the description as an example, in addition to that, the ultrasonic diagnostic system 10 can estimate an S-wave generation phase, an E-wave generation phase, a time phase in which the velocity reaches a specified velocity on the rising edge from E-wave, an A-wave generation phase, and any other phases specified by clinical characteristics.

The embodiment defines the end systole phase as the boundary phase between an S wave during a systole and an E wave during a diastole, and automatically estimates end systole phase ES from the idea of "end systole phase ES=time phase in which the motion of the heart stops=time phase in which myocardial velocity comes to zero or closest to zero".

Figure 2:
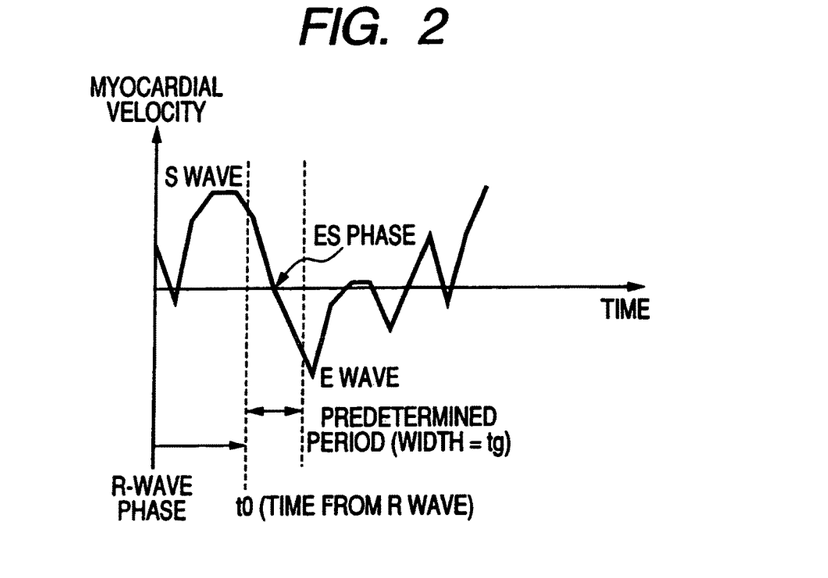
FIG. 2 is an explanatory diagram of the function of estimating end systole phase ES, showing a graph indicating the temporal changes of a myocardial velocity.

FIG. 2 is an explanatory diagram of the function of estimating end systole phase ES, showing a graph indicating the temporal changes of a myocardial velocity. As shown in FIG. 2, it is preferable that the end systole phase ES be estimated by specifying a time phase in which |myocardial velocity| comes to the minimum in a predetermined period t0 to t0+tg that is set between an S-wave phase and an E-wave phase (hereinafter, referred to as "an estimation object period").

Figure 3:
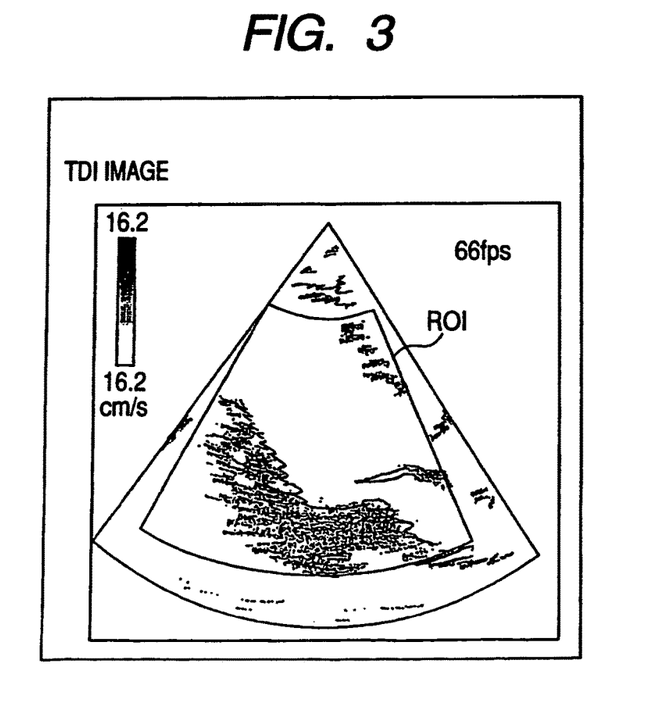
FIG. 3 is a diagram of an example of an ROI set in an ultrasonic image used for calculating a myocardial velocity.

Here, as the myocardial velocity, for example the sum of the velocities at the positions of the cardiac muscle in the ROI set in the ultrasonic image (TDI image), as shown in FIG. 3, or the sum of the absolute values of the velocities at the positions of the cardiac muscle in the ROI (that is, |velocity|) is used.

When the myocardial velocity is defined as the sum of the velocities at the positions of the cardiac muscle in the ROI, the tissue velocity of the components toward beams can be found by the tissue Doppler imaging, so that the motion of tissue may be not always small if the sum is small. However, since the velocity in this estimation is high, a time phase in which the motion of cardiac tissue stands still can be detected approximately.

On the other hand, when the myocardial velocity is defined as the sum of the velocities at the positions of the cardiac muscle in the ROI, the component of motion is added as the absolute value in all cases, so that, although complicated, a time phase in which the motion of cardiac tissue stands still can be detected more accurately.

Figure 4:
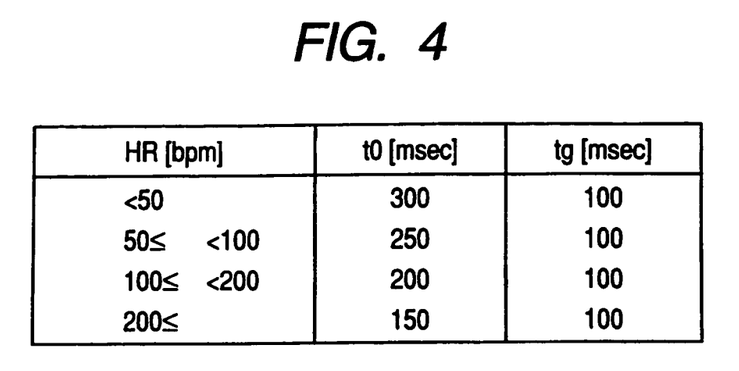
FIG. 4 is an example of a table showing the relationship among heart rates, estimation-object-period start phases (start phases), and the widths of the estimation object period from the start phase.

It is preferable that the estimation object period be controlled depending on the heart rate HR because the time per one heartbeat varies among individuals. As a specific method of controlling, it is preferable that an estimation-object-period start phase (start phase) and the width of the estimation object period from the start phase be stored in the storage unit 20 in advance as a table for heart rates, as shown in FIG. 4, and the motion-information processing unit 16 automatically determines the estimation object period on the basis of the heart rate obtained from an electrocardiogram (ECG) or input from the input unit 19 and the table. Alternatively, an integration-interval start phase by the TTI and the width of the estimation object period may be set by a predetermined function using a heart rate as a variable.

The end systole phase ES thus estimated is displayed in a specified form.

Figure 5:
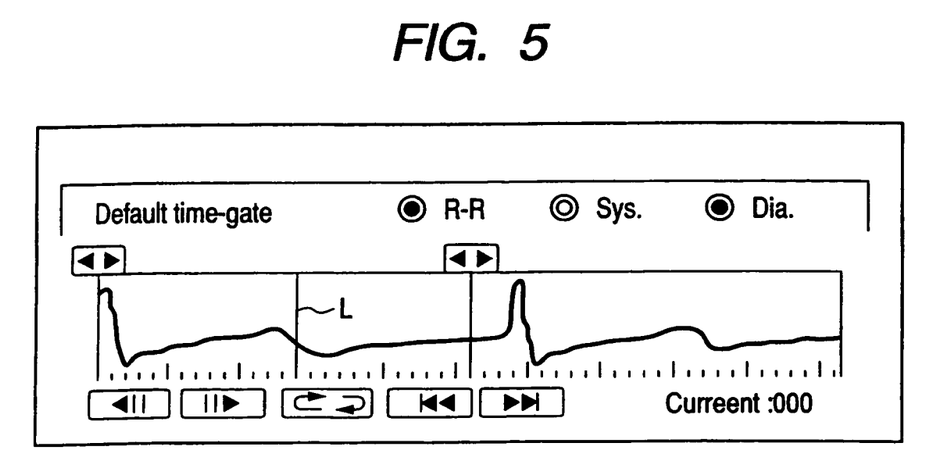
FIG. 5 is a graph of an example of the relationship between the end systole phase ES, indicated by ES-phase line, and an electrocardiographic complex.

FIG. 5 is a graph of an example of the relationship between the end systole phase ES, indicated by ES-phase line L, and an electrocardiographic complex. This allows the user to easily grasp the position of the end systole phase ES throughout the heartbeat.

(Automatic Setting of Cardiac Phase Interval as Integration Interval)

Automatic setting of a cardiac phase interval as an integration interval of the ultrasonic diagnostic system 10 will next be described. The automatic setting is for automatically setting a cardiac phase interval, which can be an integration interval when a systole, a diastole, a cardiac cycle, and other motion information are calculated by the TTI method, based on the estimated end systole phase ES and an R-wave phase found by an ECG. This allows the motion information defined by time quadrature in TTI method to be analyzed and acquired easily.

Figure 6:
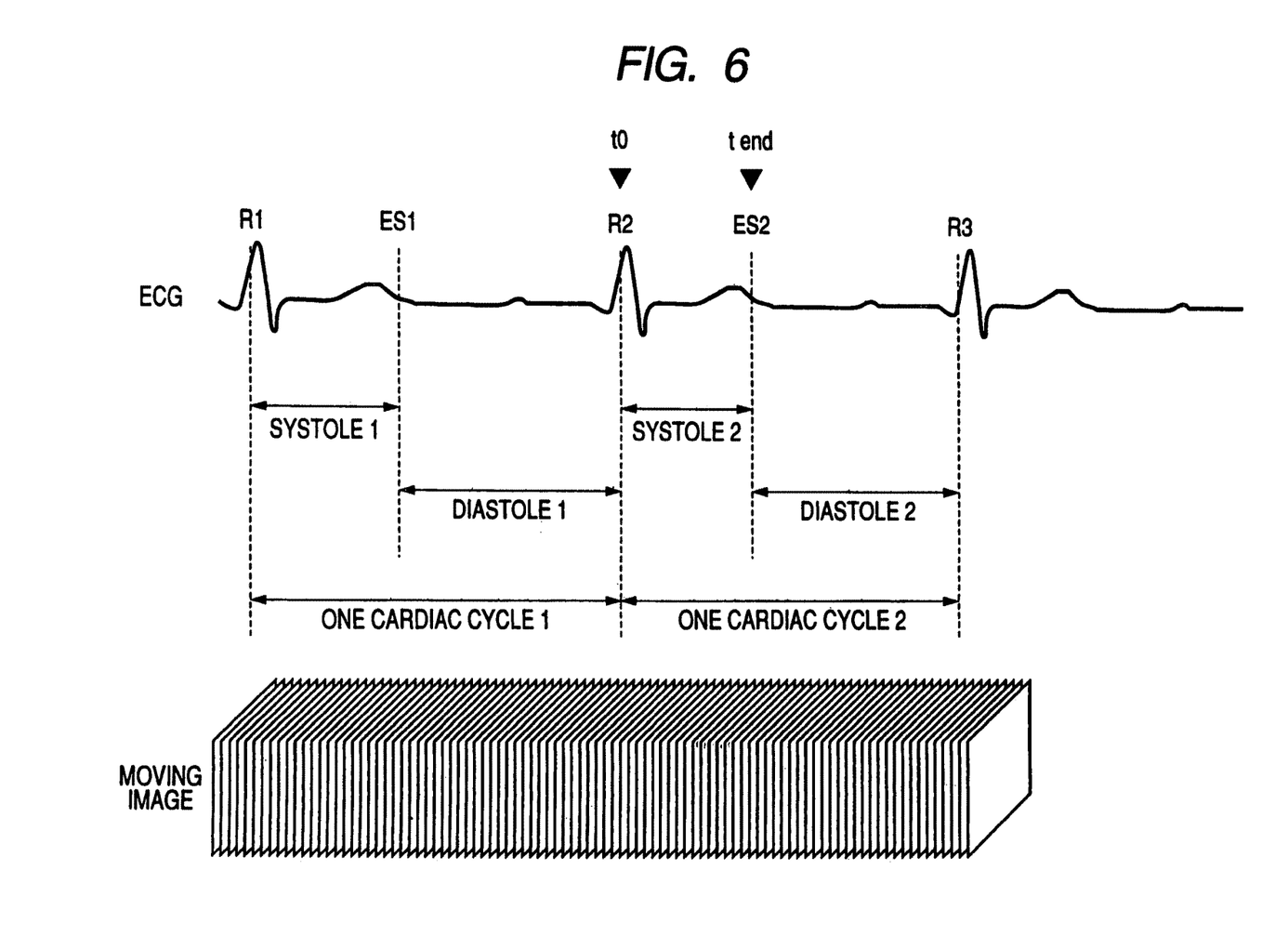
FIG. 6 is a diagram of an example in which the latest systole 2 is automatically set as an integration interval by TTI method.

FIG. 6 is a diagram of an example in which the latest systole 2 is automatically set as an integration interval by TTI method. As shown in FIG. 6, the motion-information processing unit 16 first regards the R-wave phase in each heartbeat detected by an ECG as an end diastole, and estimates the R-ES phase interval as a systole using the end diastole and the end systole phase ES obtained by the estimation, estimates the ES-R phase interval as a diastole, and estimates the R-R phase interval as one heart cycle. The motion-information processing unit 16 automatically sets the R2-wave phase that is the start phase of the latest systole 2 among the estimated phase intervals as the lower limit t0 of the integration interval, and sets the end systole phase ES2 that is the end time of the latest systole 2 as the upper limit tend of the integration interval.

Figure 7:
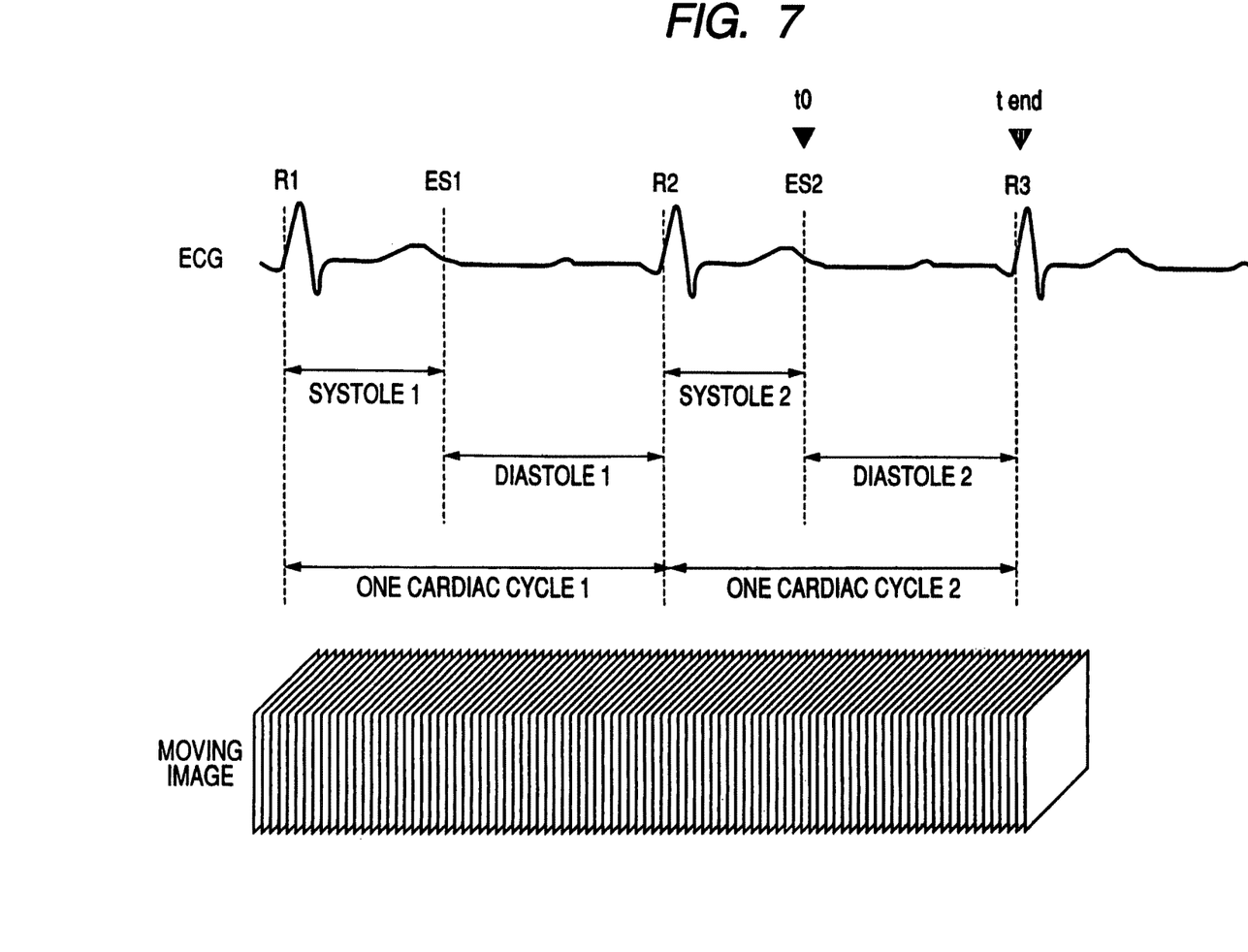
FIG. 7 is a diagram of an example in which the latest diastole 2 is automatically set as an integration interval by TTI method.

FIG. 7 is a diagram of an example in which the latest diastole 2 is automatically set as an integration interval by TTI method. As in FIG. 6, the motion-information processing unit 16 automatically sets the end systole phase ES2 that is the start phase of the latest diastole 2 among the estimated phase intervals as the lower limit t0 of the integration interval, and sets the R3-wave phase that is the end time of the latest diastole 2 as the upper limit tend of the integration interval.

Figure 8:
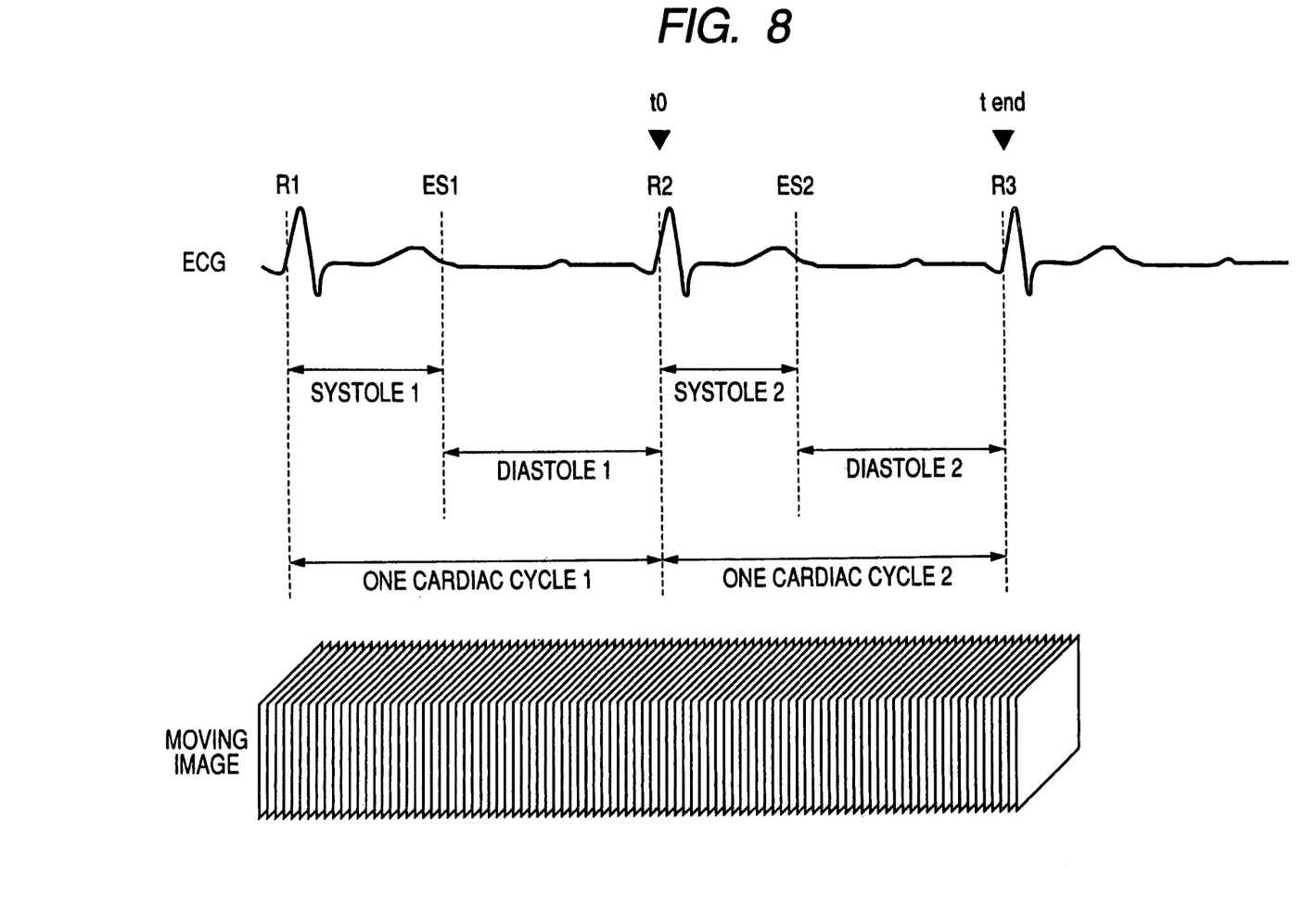
FIG. 8 is a diagram of an example in which the latest cardiac cycle is automatically set as an integration interval by TTI method.

FIG. 8 is a diagram of an example in which the latest cardiac cycle is automatically set as an integration interval by TTI method. As in FIG. 6, the motion-information processing unit 16 automatically sets the R2-wave phase that is the start phase of the latest cardiac cycle 2 among the estimated phase intervals as the lower limit t0 of the integration interval, and sets the R3-wave phase that is the end time of the latest cardiac cycle 2 as the upper limit tend of the integration interval. The one cardiac cycle may not necessarily use the R-wave generating phase as the reference, and may use the end systole phase ES or the like, for example.

The selection of the integration interval among the systole, the diastole, and the one cardiac cycle described above is executed in such a manner that the user checks one of the items "one cardiac cycle (R-R)", "systole", and "diastole", as shown in FIG. 5. Another unique application setting other than the setting of an integration interval in each selected phase interval is then automatic switching of distortion monopolar display, for example. This allows automatic optimization of not only the setting of the object interval but also other accompanying settings, depending on the object cardiac phase interval, saving the user from controlling various settings manually to increase the simplicity of the operation.

The various object cardiac phase intervals estimated by the object cardiac-phase-interval estimation process agree with actual end systole phases with high accuracy. However, if the estimated end systole phase ES has an error, the integration interval may be fine-tuned manually, e.g., with reference to the ES-phase line L on the graph shown in FIG. 5, or may be set manually to applications.

(Operation)

A series of the processes of TTI including the automatic phase estimation and the automatic integration-interval setting will be described hereinbelow.

Figure 9:
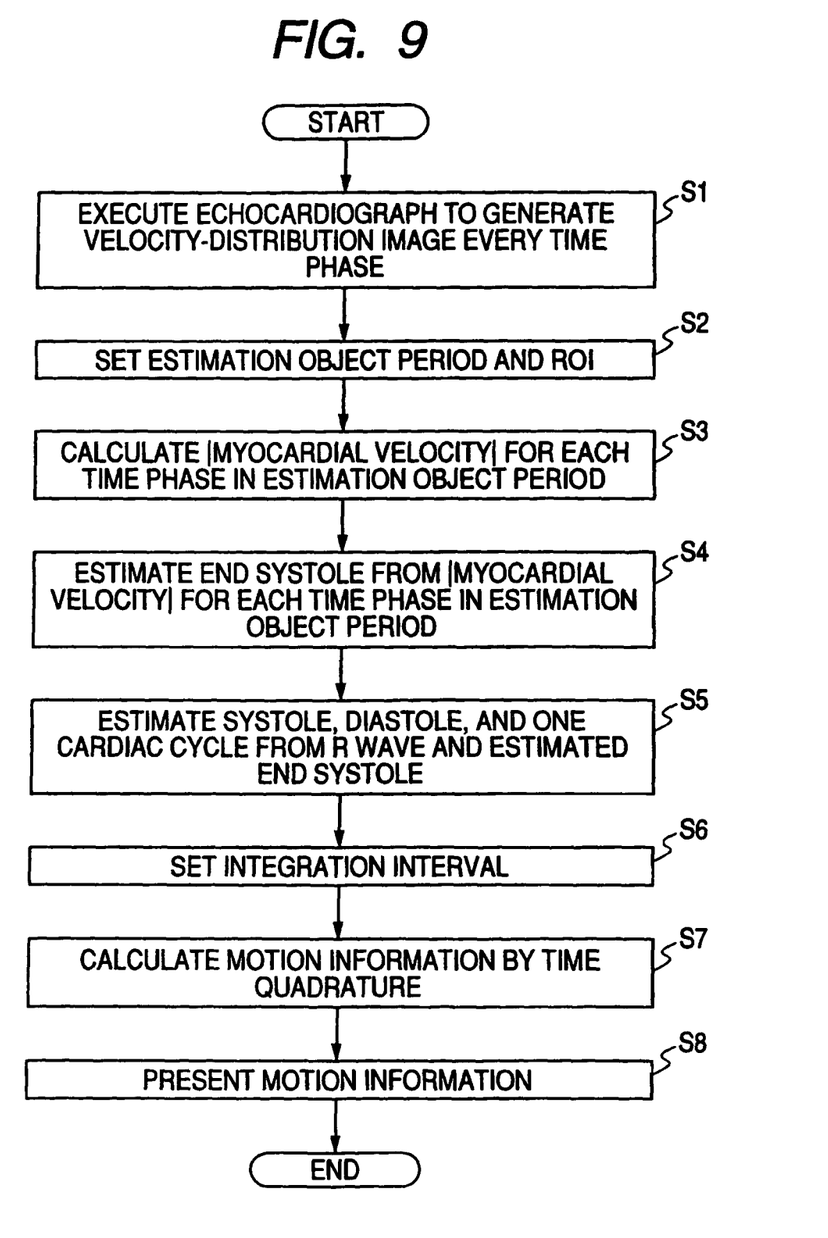
FIG. 9 is a flowchart for the procedure of a series of processes of TTI including automatic time-phase estimation.

FIG. 9 is a flowchart for the procedure of a series of processes of the TTI including automatic time-phase estimation. As shown in FIG. 9, imaging by tissue Doppler echo cardiography is executed to generate a velocity distribution image for each time phase according to obtained echo signals (step S1).

The motion-information processing unit 16 next sets an estimation object period on the basis of a heart rate HR obtained from, e.g., an electrocardiogram. Also, a region of interest for finding a myocardial velocity is set on an TDI image by the manual operation of an operator (step S2).

The motion-information processing unit 16 then calculates the absolute value of the myocardial velocity (|myocardial velocity|) for each time phase in the set estimation object period (step S3), and estimates an end systole phase (step S4).

The motion-information processing unit 16 then estimates a systole, a diastole, and one cardiac cycle from an R-wave generation phase obtained from an electrocardiogram and the estimated end systole phase (step S5), and automatically sets an integration interval on the basis of the obtained estimation result (step S6).

The motion-information processing unit 16 then executes time quadrature in the automatically set integration interval to thereby calculate cardiac motion information including a distortion, a distortion factor, and a displacement (step S7), and for example generates a distortion image in each time phase based on the result and displays it on the display unit 18 (step S8).

The foregoing structure offers the following advantages.

The ultrasonic diagnostic system allows automatic estimation of, e.g., a desired time phase, which is important clinically, using phase-to-phase velocity-distribution images. The automatic estimation can be executed in an appropriate manner using velocity information. The operator can therefore set a desired time phase necessary for examination with high accuracy and easily. This system can also achieve highly objective phase setting without variation in information due to the difference of the operator as compared with the conventional manual phase setting, thus improving the quality of diagnostic information.

The ultrasonic diagnostic system determines the integration interval of motion information defined by time quadrature in TTI method using an automatically set desired time phase. This can provide highly objective motion information in TTI method, and reduce the work of the operator in setting integration intervals. Particularly, the ultrasonic diagnostic system can automatically separate a systole and a diastole from each other using an automatically detected end systole phase and an end diastole phase that is automatically detected from an electrocardiogram. Accordingly, highly objective quantitative evaluation method by local-wall-motion indices such as distortion and displacement using a tissue velocity can be quickly achieved by a simpler operation.

The invention is not limited to the foregoing embodiment and can be embodied in an actual step by modification of the components without deviating from the gist.

(1) For example, the desired-phase estimation process and the automatic integration-interval setting process which are aforementioned can also be achieved in such a manner that programs for executing each of the processes are installed in computers (including those built in workstations, image processors, or ultrasonic diagnostic systems), and are expanded on a memory. The programs for computers to execute the technique may be distributed in the form of recording media such as magnetic disks (Floppy™ disks, hard disks, and so on), optical disks (CD-ROMs, DVDs, and so on), and semiconductor memories.

(2) In the foregoing embodiment, the time phases including a systole are estimated in response to the values on the basis of myocardial velocities and velocity changes. However, the indices for phase estimation are not limited to the myocardial velocities and velocity changes, for example a structure may be adopted in which the timing at which the velocity reaches a specified velocity during a specified period in one cardiac cycle, and the rate of velocity change (the differential coefficient of velocity waveform) are used.

(3) The foregoing embodiment has been described using a heart as an diagnostic object by way of example. However, it is to be understood that the invention is not limited to that, the desired-phase estimation function of the ultrasonic diagnostic system can be applied to the diagnosis of moving regions that cyclically repeat contraction and relaxation of carotid artery, etc.

In addition, other various inventions may be made in appropriate combination of the components disclosed in the embodiment. For example, some of the components of the embodiment may be eliminated, or some of the components of different embodiments may be combined as appropriate.

According to the embodiment, an ultrasonic diagnostic system and a system and a method for ultrasonic imaging capable of simple and high-accuracy automatic detection of end systole phases for all cross-section images used in general cardiac ultrasonic examinations as described above.

What is claimed is:

1. An ultrasonic imaging apparatus comprising:
   an ultrasonic probe configured to transmit and receive ultrasonic waves for generating ultrasonic images;
   a memory configured to store time-series velocity information obtained by using the probe on a moving region of a subject that repeats contraction and relaxation cyclically, the time-series velocity information being derived from a series of ultrasonic images obtained by using pattern matching to B-mode images for a plurality of time phases or Tissue Doppler Imaging method at different times, and the time-series velocity information including velocity values in the moving region at each time phase; and
   processing circuitry configured to
   acquire cardiac rate of the subject,
   set a predetermined period based on a predetermined operation by a user referring to the cardiac rate, the predetermined period being shorter than one heart cycle and including a predetermined time phase between a systole and a diastole,
   calculate at least one of either a sum of absolute values of the velocity values in the moving region at each time phase or an absolute value of a sum of the velocity values in the moving region at each time phase, and
   estimate the predetermined time phase in the predetermined period based on the calculation result.

2. The ultrasonic imaging apparatus according to claim 1, wherein
   the processing circuitry is configured to determine an integration interval based on the estimated time phase of the subject and calculates a time-integration at the integration interval to estimate a one cycle period of the moving region of the subject.

3. The ultrasonic imaging apparatus according to claim 1, wherein
   the processing circuitry is configured to determine an integration interval based on the estimated time phase of the subject and calculates a time-integration of the velocity information at the integration interval to estimate a distortion factor, a distortion rate, a displacement or physical quantity for a moving region of the subject.

4. The ultrasonic imaging apparatus according to claim 3, wherein
   the processing circuitry is configured to determine an integration interval by selecting at least two time phases according to a cyclic movement quantity of the moving region per unit time.

5. The ultrasonic imaging apparatus according to claim 3, wherein:
   the processing circuitry estimates, on the basis of an R-wave generating phase detected by an electrocardiogram and the time-series velocity information, start systole, end systole, start diastole, end diastole, or any desired time phase in one cycle period of the moving region.

6. The ultrasonic imaging apparatus according to claim 1, comprising:
   a display configured to display the estimated predetermined time phase in a predetermined form.

7. The ultrasonic imaging apparatus according to claim 1, wherein the processing circuitry is configured to set a region of interest, and to perform the estimation based on the time-series velocity information in the region of interest.

8. The ultrasonic imaging apparatus according to claim 7, wherein the region of interest includes at least a portion of endocardium and at least a portion of pericardium.

9. The ultrasonic imaging apparatus according to claim 1, wherein the processing circuitry is configured to perform the setting by varying an object period so that the object period shortens as the acquired cardiac rate increases.

10. The ultrasonic imaging apparatus according to claim 1, wherein the processing circuitry is configured to estimate the time phase which is at least any one of start systole phase, end systole phase, start diastole phase and end diastole phase.

11. A method for ultrasonic imaging comprising:
    using an ultrasonic probe to transmit and receive ultrasonic waves for generating ultrasonic images;
    acquiring time-series velocity information obtained by using the ultrasonic probe on a moving region of a subject that repeats contraction and relaxation cyclically, the time-series velocity information being derived from a series of ultrasonic images obtained by using pattern matching to B-mode images for a plurality of time phases or Tissue Doppler Imaging method at different times, and the time-series velocity information including velocity values in the moving region at each time phase;

acquiring cardiac rate of the subject;

setting a predetermined period based on a predetermined operation by a user referring to the cardiac rate, the predetermined period being shorter than one heart cycle and including a predetermined time phase between a systole and a diastole; and calculating at least one of either a sum of absolute values of the velocity values in the moving region at each time phase or an absolute value of a sum of the velocity values in the moving region at each time phase and estimating the predetermined time phase in the predetermined period based on the calculation result.

* * * * *